(12) United States Patent
Nakayama et al.

(10) Patent No.: US 6,202,278 B1
(45) Date of Patent: Mar. 20, 2001

(54) APPARATUS FOR AUTOMATIC PLUG REMOVAL AND METHOD THEREFOR

(75) Inventors: Naoki Nakayama, Tokyo; Akio Akiyama, Kashiwa; Fumio Goda, Toyonaka, all of (JP)

(73) Assignees: Daisen Sangyo Co., Ltd., Osaka; Mitsubishi Kagaku Bio-Clinical Laboratories, Inc., Tokyo, both of (JP)

( * ) Notice: Subject to any disclaimer, the term of this patent is extended or adjusted under 35 U.S.C. 154(b) by 0 days.

(21) Appl. No.: 09/237,116

(22) Filed: Jan. 26, 1999

(30) Foreign Application Priority Data

Feb. 12, 1998 (JP) ................................................... 10-044227

(51) Int. Cl.[7] ..................................................... B23P 19/00
(52) U.S. Cl. .......................... 29/426.3; 29/426.5; 29/235; 29/801
(58) Field of Search ................................ 29/426.1, 426.3, 29/426.5, 773, 774, 778, 791, 801, 235

(56) References Cited

U.S. PATENT DOCUMENTS

| | | | |
|---|---|---|---|
| 4,068,798 | * | 1/1978 | Rohde ................................. 29/426.5 |
| 4,217,798 | * | 8/1980 | McCarthy et al. . |
| 4,465,200 | * | 8/1984 | Percarpio . |
| 4,522,089 | * | 6/1985 | Alvi . |
| 4,704,539 | * | 11/1987 | Dequesnes et al. . |
| 4,726,264 | * | 2/1988 | Bost . |
| 4,841,818 | * | 6/1989 | Plapp et al. . |
| 5,313,858 | * | 5/1994 | Stitt . |
| 5,340,544 | * | 8/1994 | Nishikawa et al. . |
| 5,490,321 | * | 2/1996 | Kaneko . |

FOREIGN PATENT DOCUMENTS

| | | | |
|---|---|---|---|
| 0 629 858 | * | 12/1994 | (EP) . |
| 1-263558 | * | 10/1989 | (JP) . |
| 5-228379 | * | 9/1993 | (JP) . |

* cited by examiner

*Primary Examiner*—I Cuda Rosenbaum
*Assistant Examiner*—Eric Compton
(74) *Attorney, Agent, or Firm*—Akin, Gump, Strauss, Hauer & Feld, L.L.P.

(57) ABSTRACT

An automatic plug removing apparatus has a conveying section and a plug removing section and, while a plurality of containers having test samples therein and sealed with plugs are being conveyed on a batch basis, the plugs are automatically removed from the containers. The plug removing section includes a member for holding a plurality of containers in an immovable state, a member for grasping the plugs provided to the containers and then removing the plugs from the containers, the grasping member being rockable and vertically movable by driving members, and partition plates insertable into gaps between the containers to provide isolated spaces for respective containers and prevent contamination between samples. A suction block may be added to suck the air in the vicinity of upper openings of the containers to eliminate a mist of samples floating thereabout.

7 Claims, 7 Drawing Sheets

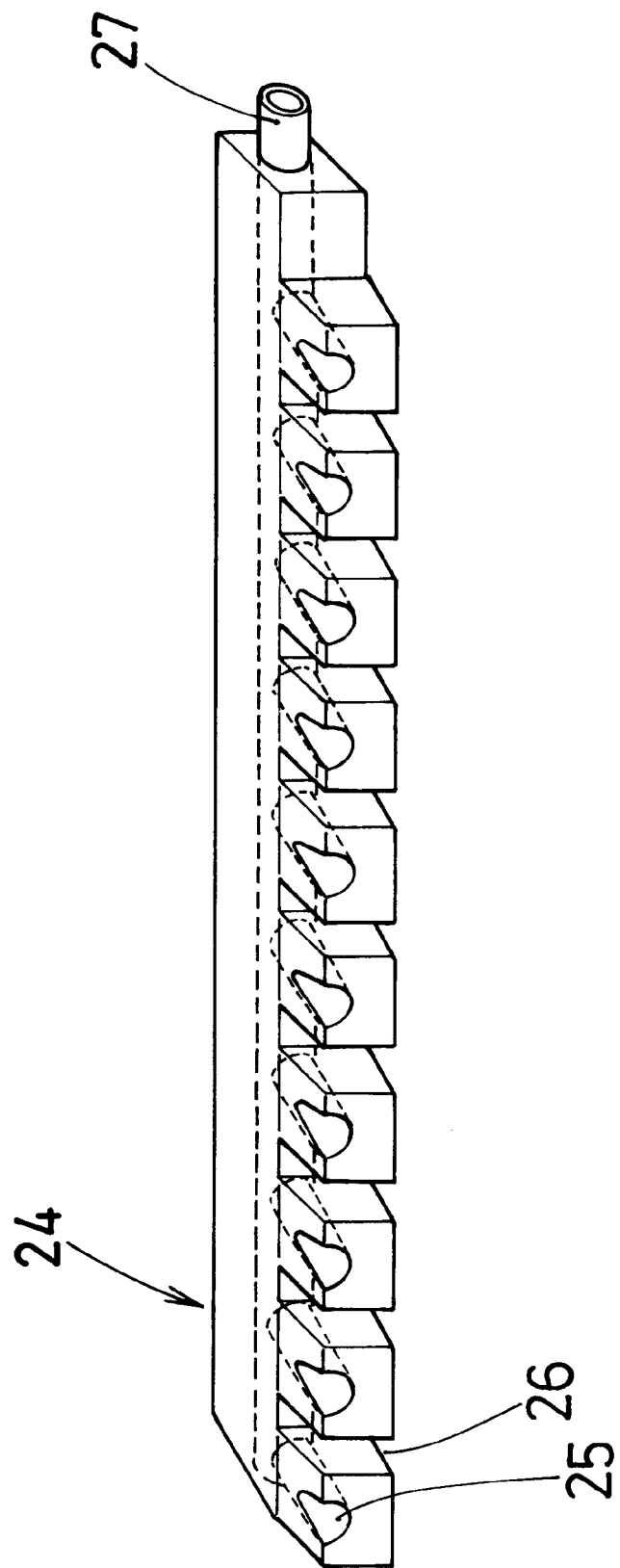

APPARATUS FOR AUTOMATIC PLUG REMOVAL AND METHOD THEREFOR

BACKGROUND OF THE INVENTION

The present invention relates to an apparatus for automatically removing sealing plugs, stoppers or caps (hereinafter referred to as plugs) from drawn blood tubes or test tubes (hereinafter referred to as containers) at the time of clinical or laboratory examination and also a method therefor.

In the field of clinical examination, open drawn blood tubes and vacuum drawn blood tubes have been widely used as containers for materials to be tested or examined such as blood (hereinafter referred to as samples). A sample drawn and collected by a syringe is in general poured into an open drawn blood tube and kept therein being closed and sealed with a plug or cap. In this case, the tube (the container) does not have to keep the the sample in a vacuumed state, and the container and plug are usually made of plastic such as polyethylene or the like. A sample that must be kept in a vacuumed state is contained in a vacuum tube, and a rubber plug or the like is used in order to stably maintain the vacuumed state within the tube for a long time.

In advance of removal of a plug from of a container for analysis, a collected sample needs to be put in a centrifuge to separate the components thereof. There have been automatic plug removing methods using apparatus as well as manual plug removal by a person's hands at work. For example, Japanese Laid-Open Patent Publication No.263558/1989 (Tokukaihei 1-263558) discloses an automatic plug removing apparatus having a cap holding down member with a recess. In this apparatus, a cap provided on a drawn blood tube is fitted into the recess of the apparatus and the cap holding down member is actuated to apply a twist and the like to the cap in the recess so as to loosen the seal between the cap and the drawn blood tube and then the cap is removed from the tube.

The centrifuging process and transportation prior to the plug removal usually cause samples to adhere to a plug on the container. Such sample adhering to the plug might scatter due to a shock at the time of removing the plug from the container or might drop down due to swinging, vibration or the like at the time of disposal. Such scatter or drops of the sample may inadvertently enter other containers and end up with contamination of samples in the other containers. As a result, correct analysis for the respective samples can not be obtained even if high-accuracy analysis is conducted. Such contamination causes a serious error in the results of clinical examination and the like, and therefore must be absolutely avoided.

Manual plug removal by a person at work tends to cause injury, infection to the person due to the scatter of samples, and contamination of samples in other containers.

In order to avoid scattering and splashing of samples, some of conventional automatic plug removing apparatus provide improved arrangements. For example, one gives a twist or a circular arc oscillating movement to a plug and then removes it from a container with a lighter force, or another reduces a plug removing speed just before a plug is removed away from a container. There is another apparatus which has a dish for receiving and collecting liquid drops from a plug in order to prevent inadvertent sample drops at the time of disposing the plug. However, these conventional apparatus fail to prevent samples from scattering or splashing completely. Especially when a plurality of containers are simultaneously put under the plug removing process on a batch basis, complete prevention of contamination cannot be obtained by the conventional apparatus.

SUMMARY OF THE INVENTION

It is an object of the present invention to provide an apparatus for automatically removing plugs from containers without contamination between samples in the containers and a method therefor.

The apparatus of the present invention is an automatic plug removing apparatus having a conveying section and a plug removing section, in which, while a plurality of containers sealed with plugs are being conveyed on a batch basis, the plugs are automatically removed from the containers. The plug removing section includes a holding means for holding a plurality of containers with plugs in an immovable state, a grasping means for grasping the plugs provided to the containers and then removing them from the containers, driving means for rocking and vertically moving the plug grasping means, and partition plates which are insertable into gaps between the plurality of containers. The apparatus may further includes an adjusting mechanism for the level of containers so as to allow the plug removing process to be done irrespective of the length of the containers on the batch. Furthermore, the apparatus may include a suction block which is positioned in the vicinity of the upper openings of the containers at the time of the plug removing process.

The method for automatic plug removal during conveyance of the present invention includes a prerequisite step of providing a plurality of containers sealed with a plurality of plugs on a conveying section on a batch basis, a first step of holding the plurality of containers with plugs in an immovable state, a second step of grasping the plugs which seal the containers, a third step of inserting partition plates into gaps between the plurality containers, and a fourth step of loosening the seal between the plugs and the containers and then lifting the plugs up to remove them from the containers. Here, the second and the third step are done in random order after the first and before the fourth step.

The above and other objects, features and advantages of the present invention will become apparent from the following description in conjunction with the accompanying drawings.

BRIEF DESCRIPTION OF THE SEVERAL VIEWS OF THE DRAWINGS

FIG. 7 is a perspective view of a suction block.

DETAILED DESCRIPTION OF THE INVENTION

Figure 1:
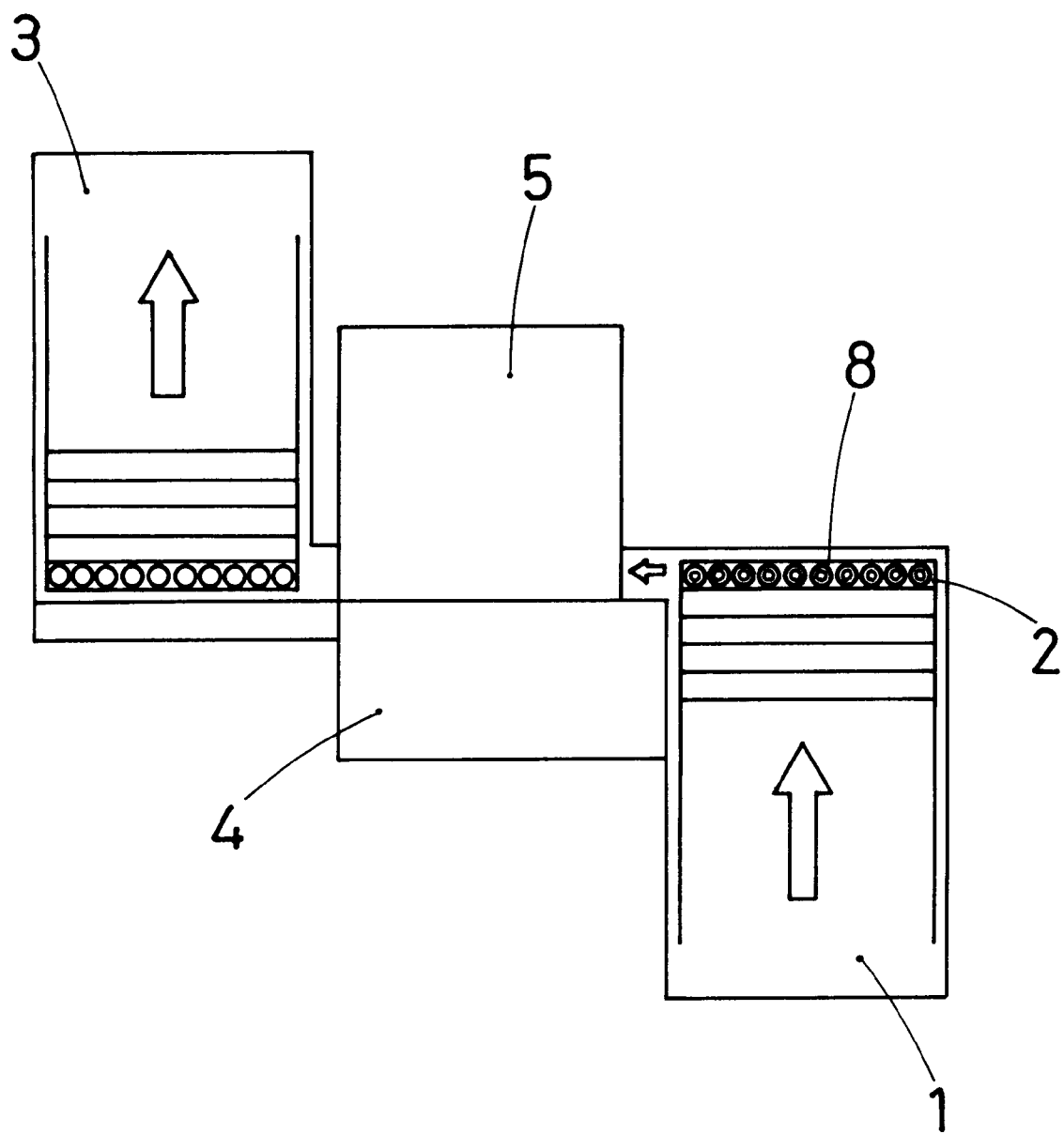
FIG. 1 is a schematic plan view of the whole system of an automatic plug removing apparatus of the present invention.

An automatic plug removing apparatus of the present invention includes a means for holding a plurality of containers 8 in an immovable state, such as a clamp 11; a means for grasping plugs 9 that seal the containers 8, such as a plug chuck 14; driving means 16 and 17 for driving the grasping means 14; and partition plates 12 that can be removably inserted between the plural containers 8. In the automatic plug removing apparatus of the present invention, the operation is carried out on a rack basis (batch basis) in which a rack receives a plurality of containers 8, and during the plug removing process the plural plugs 9 are removed from the containers 8 at the same time.

A flow of processes in which the containers 8 sealed with the plugs 9 are sent to a plug removing section 5, the plugs 9 are removed from the containers 8, and thus unplugged containers 8 are discharged can be understood in FIG. 1. This drawing shows that one rack 2 receives ten containers 8, but this is not limitative and any number of containers may be received in one rack.

First, ten containers 8 which have test samples therein and are sealed by plugs 9 are placed in a rack 2 and put on a start yard (an upstream conveying section) 1. Next, the rack 2 with the containers 8 is conveyed on the start yard 1 in an arrow direction (an upward direction in FIG. 1) down to an end of the start yard 1. At this end, the rack 2 changes its flow direction to a lateral direction indicated by an arrow and reaches to the plug removing section 5. After the plugs 9 having been removed from the containers 8 at the plug removing section 5, the rack 2 is further transported in the lateral direction to a discharging yard (a downstream conveying section) 3. The rack 2 again changes its flow direction and advances in an arrow direction (an upward direction in FIG. 1). On one side of the plug removing section 5 is provided a plug dumping box 4.

The function of respective members of the apparatus is described in accordance with the processing sequence of the containers 8.

Figure 2:
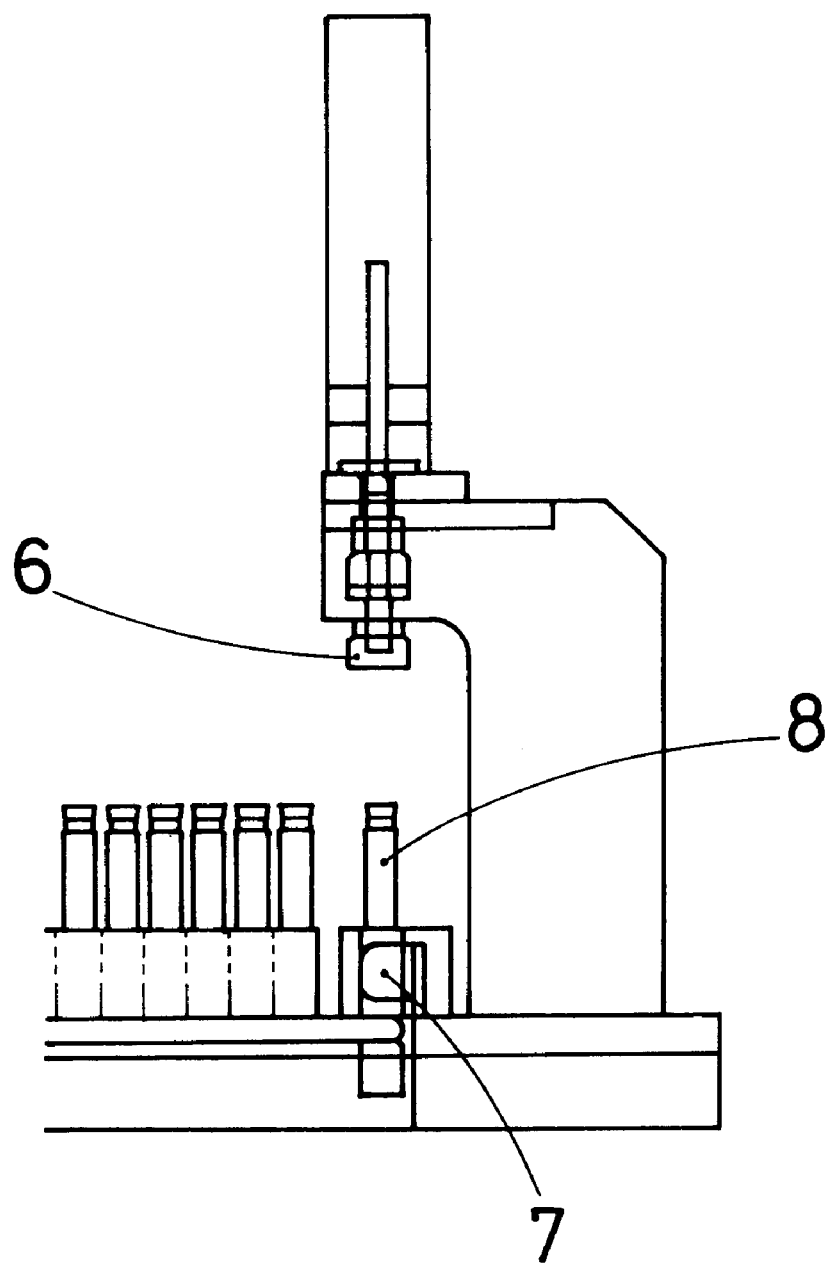
FIG. 2 is a side view of a height measuring section for containers.

A height measuring device 6 for containers 8 in a rack as shown in FIG. 2 is provided at the downstream end of the start yard 1. When the rack 2 reaches the end of the start yard 1, the height measuring device 6 comes down and measures the height of the containers 8. After the measurement, the rack 2 is forwarded to the plug removing section 5 by a rack forwarding mechanism 7. This height measuring device 6 and a height adjusting mechanism 10 (described later) collaborate to adjust the level of the plugs 9 of the containers 8. And, therefore, even if the length of containers 8 is different in each rack 2, as long as the containers in the same rack 2 have the same length, the plug removing process can be conducted at the plug removing section 5 without any problem.

Figure 3:
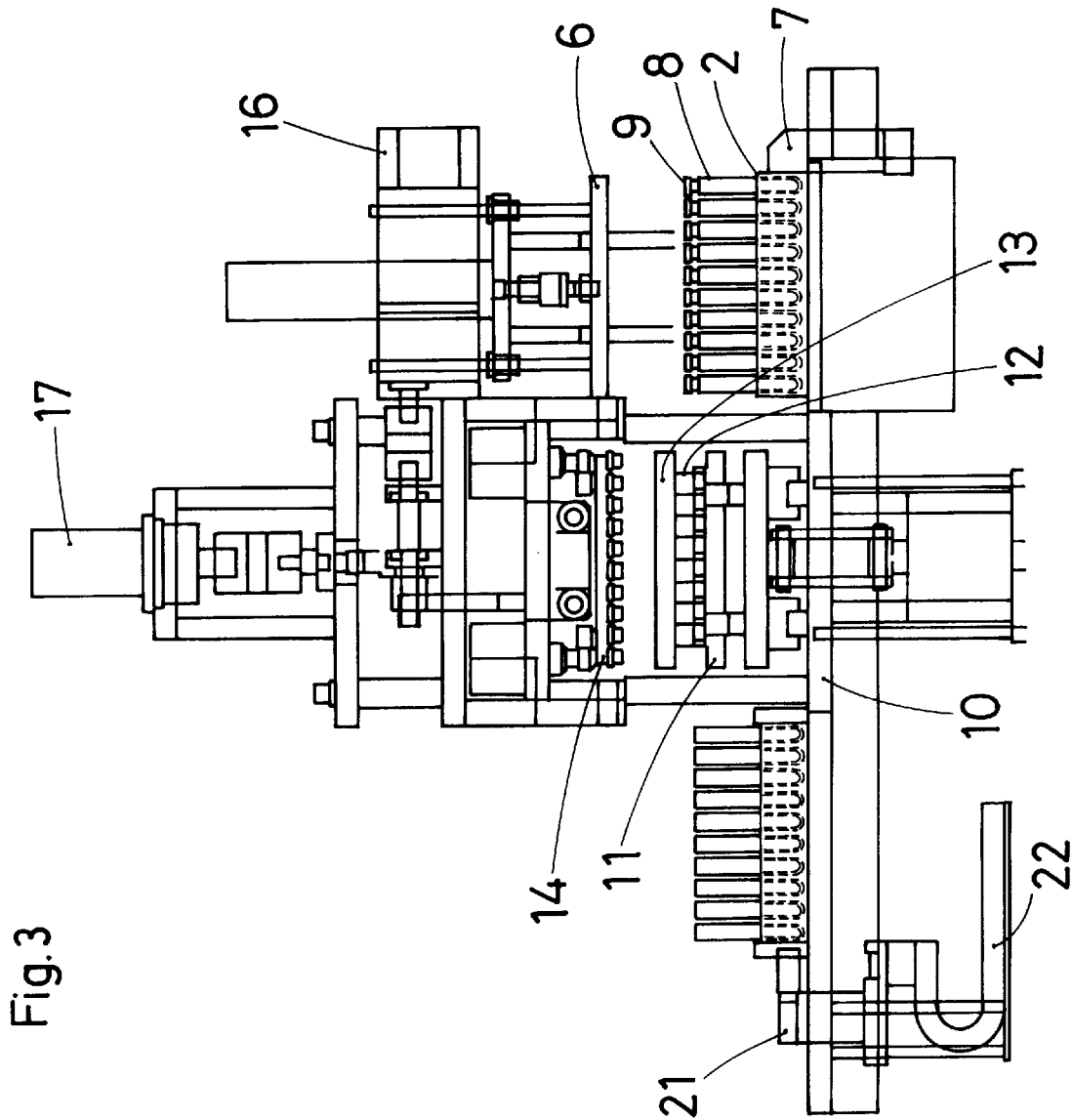
FIG. 3 is a front view of the automatic plug removing apparatus of the present invention.
Figure 4:
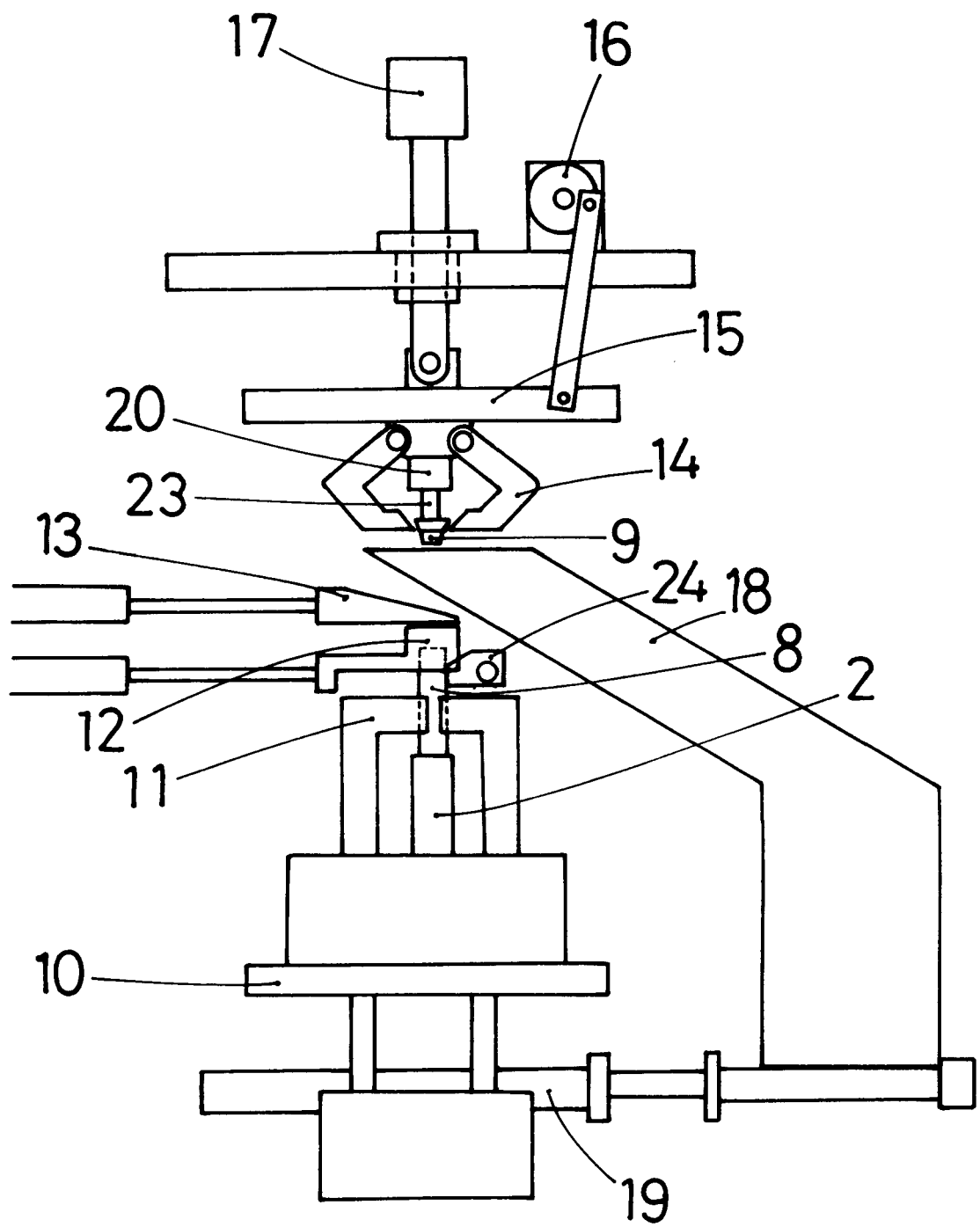
FIG. 4 is a side view of the automatic plug removing apparatus of the present invention.

FIG. 3 is a front view of the automatic plug removing apparatus in which one rack 2 having plugged containers 8 is located at the end of the start yard 1, another rack having unplugged containers are on the discharge yard, and the plug removing section 5 is empty. FIG. 4 is a side view of the automatic plug removing apparatus in which one rack 2 is placed at the plug removing section 5, plugs 9 have been removed from containers 8, and a liquid drop receiving dish 13 and a plug dumping chute 18 are located under the removed plugs 9. Referring to these two drawings, the movement of respective members of the apparatus is described.

The height adjusting mechanism 10 functions in response to data from the height measuring device 6. In case a rack 2 having shorter containers 8 comes in, the height adjusting mechanism 10 raises the rack 2, while in case another rack having longer containers 8 comes in, it lowers the rack 2, and adjusts the height of plugs 9 to a level where a plug chuck reliably grasps respective plugs. With this mechanism, the plug chuck 14 as the plug grasping means may always work at the same level.

A plurality of containers 8 in a rack 2, the number of which is ten in this case, are supported and held immovably at the same time by a clump 11 as the container holding means. Next, partition plates 12 advance into respective nine gaps between the ten containers 8. These partition plates 12 isolate the respective containers 8 so as not to cause contamination of the samples therein in spite of sample scattering at the time of removal of plugs described below.

The plug removing process is carried out by a rocking motor 16 and a vertical motion motor 17. The rocking motor 16 moves a rocking plate 15 which is provided with the plug chuck 14 and an upper plate 20. The upper plate 20 is provided with plug pressing members 23. The vertical motion motor 17, which is also connected to the rocking plate 15, raises and lowers the plug chuck 14, the upper plate 20 and the plug pressing members 23 together with the rocking plate 15, and also opens and closes the plug chuck 14 provided on the rocking plate 15.

First, the vertical motion motor 17 actuates the rocking plate 15 to lower down to a predetermined level, at this level the plug chuck 14 provided on the rocking plate 15 is closed so as to grasp the plural plugs 9 at once. The rocking motor 16 subsequently actuates the rocking plate 15 to oscillate up and down, thereby allowing the plug chuck 14 attached to the rocking plate 15 to oscillate responsively. According to this oscillation, the plugs 9, gripped by the plug chuck 14 from opposite sides, slide up and down on the inner walls of the containers 8 in opposite directions on the opposite sides. And consequently the plugs 9 become out of the sealing state in the containers to be loosened. In this state, the vertical motion motor 17 actuates the rocking plate 15 and the plug chuck 14 to rise up, and the plugs 9 held by the plug chuck 14 are pulled up and removed from the containers held by the clamp 11. The movement of the rocking plate 15 due to the rocking motor 16 while the plug chuck 14 grasps the plugs 9 may be set in one direction (i.e. in FIG. 4, the right side of the rocking plate 15 is moved only upward or only downward), or may be set in repetitious up and down movements. The latter allows easier removal of the plugs 9 from the containers 8 and a smaller shock at the time of removal.

Figure 6:
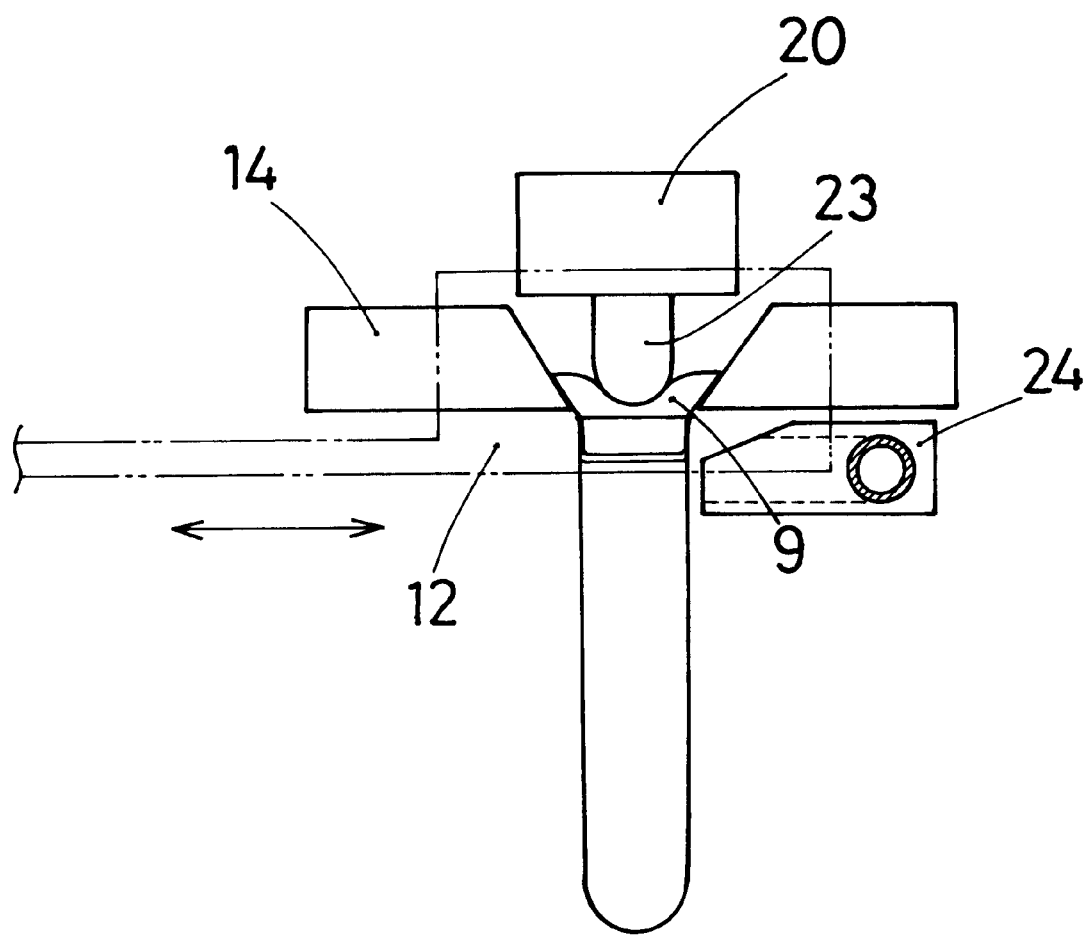
FIG. 6 is a side view showing relationship between the partition plates and the surrounding members.

Each plug pressing member 23 is provided to the rocking plate 15 having the upper plate 20 therebetween. When the plug chuck 14 grasps the respective plugs 9 at their outer circumferential walls, the plug pressing members 23 press their top faces. Therefore in case rubber plugs, as shown in FIG. 6, this results in reducing deformation of the plugs 9 and ensuring reliable grasping and holding of the plugs 9. The plug removing apparatus of the present invention may also apply to plugs of other material such as plastic.

In this embodiment, a servo motor is used as the vertical motion motor 17, the raising speed of plugs 9 is set to be reduced immediately before the plug removal (just before the plugs 9 come off the containers 8). With this set-up of the mechanism, scattering of samples is reduced to a minimum.

Figure 5:
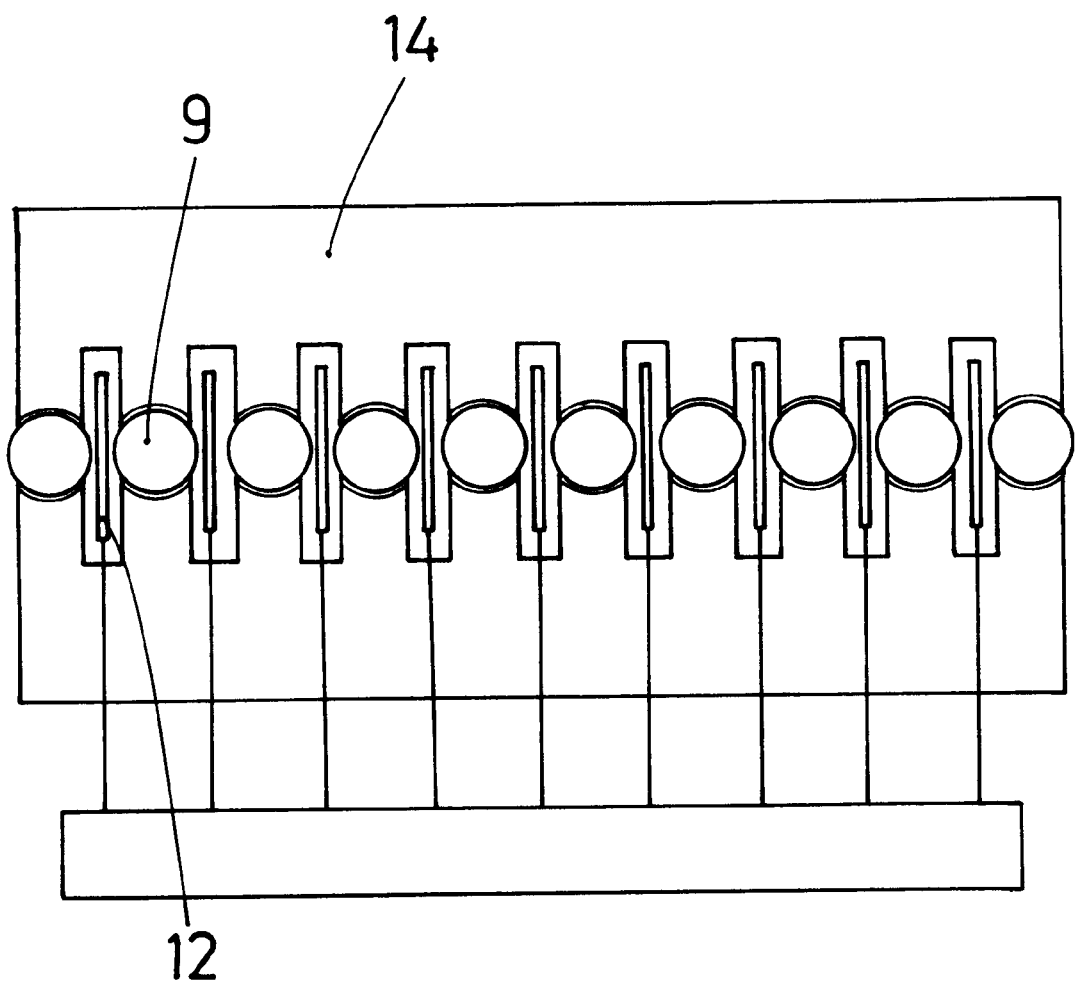
FIG. 5 is a plan view showing relationship between partition plates and their surrounding members.

In FIGS. 5 and 6, the plug chuck 14 grasps the plugs 9 and the partition plates 12 are inserted into the respective gaps between the containers 8. As seen from FIG. 5, each partition plate 12 is located between both (upper and lower in the drawing) gripping members of the plug chuck 14, and, as seen from FIG. 6, extended to a level higher than the top level of the containers 8. With this constitution, the gaps between the plugs 9 of the adjacent containers 8 (the gaps in a lateral direction of FIG. 5) are separated by partition plates 12 up to a rather high level.

Therefore, the partition plates provide an isolated space in the vicinity of the top opening of each container 8 so that even if scattering of samples occurs, it is possible to prevent the scattered samples from erroneously entering the adjacent containers, and consequently to prevent contamination due to the scatter of the samples.

In a more preferred embodiment, a suction block 24, shown in FIG. 7, is provided in addition to the above-mentioned partition plates 12. The suction block 24 has a shape as shown in FIG. 7. The front side which faces the containers 8 is provided with recesses 25 at positions corresponding to the respective containers 8 and cut-out sections 26 at positions corresponding to the respective partition plates 12. Each recess 25 has a hole in its inward back which is connected to an air hose 27 that extends in the longitudinal direction of the suction block 24. Each of the cut-out sections 26 of the suction block 24 receives one portion of each partition plate 12. Therefore, whether the suction block 24 is used or not, the space in the vicinity of the top opening of each container 8 is isolated by the partition plates 12 at the time of removal of the plugs from the containers 8.

As shown in FIG. 6, the suction block 24 is placed in the vicinity of the top openings of the containers 8. When the plugs 9 have been pulled out from the containers 8, the outer air rapidly flows into the containers 8, or abruptly mixes with air inside the containers 8. As a result, portions of the samples tend to become mist and spread and float in the vicinity of the openings of the containers 8. In order to prevent such a mist of the samples from contaminating other samples, the first embodiment is provided with the partition plates 12 for separating the space between the adjacent containers 8. However, there is a possibility that such mist of the samples might still cause contamination of the other samples in the adjacent containers 8. Here, by sucking air through the recesses 25 of the suction block 24 at the time of removing the plugs, the mist of samples floating in the air is sucked away so as to completely prevent the contamination.

Referring back to FIG. 4, after the plugs 9 are removed from the containers 8 held by the clamp 11, the liquid drop receiving dish 13 quickly advances between the removed plugs 9 and the containers 8, and receives and collects liquid drops from the plugs 9 so as to prevent them from entering other containers 8.

Next, the plug dumpling chute 18 is shifted between the removed plugs 9 and the containers 8, and the plug chuck 14 opens and releases the removed plugs 9 into the plug dumping chute 18. In order to secure release of the removed plugs 9 which might remain sticking to the plug pressing member 23, a driving mechanism (not shown) may be provided. This mechanism actuates the plug pressing members 23 to retract into the upper plate 20 and lets them release the plugs 9 securely.

Subsequently the plugs 9 drop into the plug dumping chute 18 and are guided to and collected in the plug dumping box 4 shown in FIG. 1. The plug dumping chute 18 and the plug dumping box 4 are detachable from the main system for easy cleaning, collection of dumped plugs and other maintenance purposes.

Afterwards, the rack carrying the unplugged containers 8 is caught by a rack chuck 21 shown in FIG. 3, shifted by a rack drawing member 22 to the discharge yard 3 shown in FIG. 1. Such racks are accumulated there and conveyed forward in due course. On the other hand, the plug removing section 5 receives subsequent racks 2 carrying plugged containers 8 one after another, and repeats the same plug removing process.

During the automatic plug removing process according to the present invention, the partition plates 12 are located between the adjacent containers so as to separate the space between the top openings of the containers and isolate respective separated spaces. This prevents contamination of samples in respective containers to be examined and therefore correct examination results can be obtained from the uncontaminated samples. Moreover, addition of the suction block 24 allows to suck and eliminate a mist of samples floating around the openings of the containers due to plug removal. This results in complete prevention of contamination and more highly reliable examination results can be obtained.

We claim:

1. An automatic plug removing apparatus having a conveying section and a plug removing section, in which, while a plurality of containers having test samples therein and sealed with plugs are being conveyed on a batch basis, the plugs are automatically removed from the containers, the plug removing section comprising:

a holding means for holding a plurality of containers sealed with plugs in an immovable state;

a grasping means for grasping said plugs provided to said containers and then removing said plugs from said containers;

driving means for rocking and vertically moving said plug grasping means; and partition plates which are insertable into gaps between said plurality of containers.

2. An automatic plug removing apparatus according to claim 1, further comprising a level adjusting mechanism for said containers sealed with said plugs so that said plugs are grasped by said grasping means.

3. An automatic plug removing apparatus according to claim 1 further comprising a suction block which is positioned in the vicinity of upper openings of said containers in said plug removing section.

4. An automatic plug removing apparatus according to claim 3 wherein said suction block comprises a plurality of cut-out sections which are receivable of said respective partition plates.

5. A method for automatic plug removal during conveyance comprising:

a prerequisite step of providing a plurality of containers having test samples therein and sealed with a plurality of plugs on a conveying section on a batch basis;

a first step of holding said plurality of containers as a batch basis in an immovable state;

a second step of grasping said plugs which seal said containers;

a third step of inserting partition plates into gaps between said plurality of containers;

a fourth step of loosening the seal between said plugs and said containers and then pulling up said plugs to remove from said containers; and wherein said second and said third steps are done in random order after said first and before said fourth step.

6. A method according to claim 5 wherein said loosening process in said fourth step includes rocking of a plug grasping member upward and downward.

7. A method according to claim 5 further comprising a fifth step of sucking air around openings of unplugged containers during and/or after said fourth step.

* * * * *